US008535904B2

(12) United States Patent
Kuroda et al.

(10) Patent No.: US 8,535,904 B2
(45) Date of Patent: Sep. 17, 2013

(54) METHOD OF ENHANCING SKIN BARRIER FUNCTION

(75) Inventors: Shohei Kuroda, Yokohama (JP);
Takuya Yamamoto, Yokohama (JP);
Yuko Saeki, Yokohama (JP); Masumi Kurasawa, Yokohama (JP)

(73) Assignee: Pola Chemical Industries Inc., Shizuoka-Shi, Shizuoka (JP)

( * ) Notice: Subject to any disclaimer, the term of this patent is extended or adjusted under 35 U.S.C. 154(b) by 0 days.

(21) Appl. No.: 13/476,868

(22) Filed: May 21, 2012

(65) Prior Publication Data

US 2012/0282357 A1    Nov. 8, 2012

Related U.S. Application Data

(62) Division of application No. 12/516,483, filed as application No. PCT/JP2007/074070 on Dec. 7, 2007, now abandoned.

(30) Foreign Application Priority Data

Dec. 8, 2006 (JP) ................................. 2006-331294
May 21, 2007 (JP) ................................. 2007-133776

(51) Int. Cl.
*C12Q 1/02* (2006.01)
*A61K 38/00* (2006.01)

(52) U.S. Cl.
USPC .......................................... 435/29; 514/18.6

(58) Field of Classification Search
USPC .......................................... 435/29; 514/18.6
See application file for complete search history.

(56) References Cited

U.S. PATENT DOCUMENTS

| 6,395,286 | B1 * | 5/2002 | Pillai et al. ............... 424/401 |
| 6,682,763 | B2 * | 1/2004 | Kuno et al. ............... 424/769 |
| 7,169,609 | B2 | 1/2007 | Negulescu et al. |
| 8,101,162 | B2 * | 1/2012 | Shimada et al. ............ 424/70.1 |
| 2004/0092855 | A1 | 5/2004 | Fabo |
| 2005/0100519 | A1 * | 5/2005 | Guth et al. ................ 424/62 |
| 2005/0106116 | A1 * | 5/2005 | Smothers ................. 424/70.1 |

FOREIGN PATENT DOCUMENTS

| JP | 11-029460 A | 2/1999 |
| JP | 10172310 | * 1/2000 |
| JP | 2007-174931 | 7/2007 |

OTHER PUBLICATIONS

Sally Hansen "Airbrush Legs Lotion" (http://sallyhansen.com/products/skin-body/leg-care/airbrush-legs-lotion).*
HairBoutique.com (http://talk.hairboutique.com/printer_friendly_posts.asp?TID=20669).*
Kuroda, et al. "Tight Junctions are Involved in Intercellular Divalent Cation Permeability in Cultured Normal Human Epidermal Keratinocytes," *Journal of Investigative Dermatology*, vol. 127, No. Suppl. 1, p. S66, Apr. 2007.
Denda, et al. "Skin Surface Electric Potential Induced by Ion-Flux through Epidermal Cell Layers," *Biochemical and Biophysical Research Communications*, vol. 284, No. 1, pp. 112-117, Jun. 1, 2001.
Vičanová, et al. "Normalization of Epidermal Calcium Distribution Profile in Reconstructed Human Epidermis is Related to Improvement of Terminal Differentiation and Stratum Corneum Barrier Formation," *Journal of Investigative Dermatology*, vol. 111, No. 1, pp. 97-106, Jul. 1998.
"Abstracts for the 31$^{st}$ Annual Meeting of the Japanese Society for Investigative Dermatology, May 31-Jun. 2, 2006, Kyoto, Japan" *Journal of Dermatological Science*, pp. 133-198, vol. 42, No. 2, May 2006.
Ma, et al. "Mechanism of Extracellular Calcium Regulation of Intestinal Epithelial Tight Junction Permeability: Role of Cytoskeletal Involvement," *Microscopy Research and Technique*, vol. 51, No. 2, pp. 156-168, Oct. 15, 2000.
Hwang, et al. "Role of Scarf and its Binding Target Proteins in Epidermal Calcium Homeostasis," *The Journal of Biological Chemistry*, vol. 282, No. 25, pp. 18645-18653, Jun. 22, 2007.
Ahn, et al. "Role of PKC-Delta as a Signal Mediator in Epidermal Barrier Homeostasis," *Arch Dermatol Res.*, vol. 299, pp. 53-57, 2007.
Yuki, et al. "Tight Junction Proteins in Keratinocytes:" Localization and Contribution to Barrier Function, *Experimental Dermatology*, vol. 16, pp. 324-330, 2007.
Yuki et al., "Effects of calcium concentration on development of tight junction in normal human keratinocytes," *Journal of Dermatological Science*, vol. 42(2), pp. 138-139 (2006).

* cited by examiner

*Primary Examiner* — Karen Cochrane Carlson
*Assistant Examiner* — Natalie Moss
(74) *Attorney, Agent, or Firm* — Knobbe, Martens, Olson & Bear LLP (57) ABSTRACT

A method for adjusting calcium ion in epidermis is described. The method involves applying a material for enhancing skin barrier function to the skin of a subject. Appropriate materials include *Pimpinella* extract, *Asteroidea* extract, L-Carnitine, Royal jelly hydrolysate, Pellicer, Palmaria extract, ε, γ-Glutamyl lysine, *Coptis japonica* extract and *citrus aurantium* peel extract

1 Claim, 8 Drawing Sheets

METHOD OF ENHANCING SKIN BARRIER FUNCTION

CROSS-REFERENCE TO RELATED APPLICATIONS

This application is a divisional of U.S. application Ser. No. 12/516,483, filed May 27, 2009, which is incorporated herein by reference and which is the U.S. National Phase under 35 U.S.C. §371 of International Application PCT/JP2007/074070, filed Dec. 7, 2007, which claims priority to JP 2006-331294, filed Dec. 8, 2006 and JP 2007-133776, filed May 21, 2007.

TECHNICAL FIELD

The present invention relates to a method of evaluating skin barrier function, a method of screening material for enhancing skin barrier function using the evaluating method, the material for enhancing skin barrier function, and a cosmetic containing the material for enhancing skin barrier function.

BACKGROUND ART

At present days, patients who suffer from skin diseases due to skin barrier dysfunction, such as a high incidence of atopic dermatitis, have increased rapidly. This is considered to be caused by an excessive increase in stress (see, for example, Patent Documents 1, 2, 3, and 4). In fact, there is a high incidence of the skin barrier dysfunction, so it is required to develop means for preventing a disease in an early stage from becoming severe or means for ameliorating an actual symptom.

However, in many cases, expression of the skin barrier dysfunction described above is liable to be recognized after developments of severe symptoms such as an occurrence of skin roughness and a rapid increase in amount of transepidermal water loss. Accordingly, it can be said that the development of means for detecting such skin barrier dysfunction in an early stage has been desired.

There are some proposals on animal models for skin barrier dysfunction (see, for example, Patent Documents 5 and 6), but in all the proposals, animals must be used and much time and efforts are required. Further, there is a room for doubt about its reproducibility. Moreover, in such screening using animal models, the number of test samples to be evaluated is limited.

There has not been known at all a method of evaluating skin barrier function using culture cells.

Meanwhile, there has been known that a calcium ion is involved in differentiation/maturation of epidermal/horny layer cells, and that presence of an appropriate amount of the calcium ion gives order to differentiation/maturation of epidermal/horny layer cells. Also, there has been known that an appropriate concentration gradient of the calcium ion from a lower layer of an epidermis toward an upper layer thereof provides a function of constructing a sufficient barrier structure. However, there has been also known that the excessive calcium ion impairs the skin barrier function (see, for example, Non-patent Documents 1, 2, and 3). Moreover, a technology for adjusting the concentration of a metal ion such as a calcium ion in the skin has not been known at all.

[Patent Citation 1] JP 2002-291909 A
[Patent Citation 2] JP 2000-159666 A
[Patent Citation 3] JP 2000-035425 A
[Patent Citation 4] JP 10-279505 A
[Patent Citation 5] JP 2001-321016 A
[Patent Citation 6] WO 2003/053466
[Non Patent Citation 1] Hwang J. et al, J Biol. Chem., (2007), in print
[Non Patent Citation 2] Ahn B K. et al, Arch Dermatol Res., 2007; 299(2): 53-7
[Non Patent Citation 3] Yuki T. et al, Experimental Dermatology, 2007; 16(4), 324-330

DISCLOSURE OF INVENTION

The present invention has been made under the above-mentioned circumstances, and it is an object of the present invention to provide a technology for developing an excellent material for enhancing skin barrier function, and to develop and provide a cosmetic having excellent ability to enhance the skin barrier function based on the technology.

In view of the above-mentioned circumstances, the inventors of the present invention found that a material for enhancing skin barrier function that is excellent as a cosmetic material can be obtained by screening the material using movement of metal ions as an index, in particular, calcium ions that affect differentiation of a horny layer cell, from dermis or tissue equivalent for the dermis to horny layer cell, and thus completed the present invention. That is, the present invention is as follows.

(1) A method of evaluating skin barrier function, comprising:
using permeability of metal ions through an epidermal cell layer as an index, and evaluating that the higher the permeability of the metal ions, the lower the skin barrier function.

(2) The method of evaluating skin barrier function according to (1), wherein a type of the metal ions is calcium ion and/or magnesium ion.

(3) A method of screening material for enhancing skin barrier function, comprising:
1) culturing normal human epidermal cells in wells with a semipermeable membrane bottom, in presence and absence of a test substance;
2) adding a medium not containing metal ions to be measured to the above of cells in each well and a medium containing the metal ions to be measured to the below of the cells in each well, provided that the below is a side where the cells are adhered to the semipermeable membrane, and the above is an opposite side thereto, and culturing the cells;
3) measuring a concentration of the metal ions in each medium; and
4) calculating permeability of the metal ions in an epidermal cell layer based on the measured concentrations of the media, discriminating that the test substance is effective as the material for enhancing skin barrier function in a case where the permeability is reduced in the medium in which the test substance is added compared to the permeability in the medium in which no test substance is added, and evaluating that the larger the level of reduced permeability, the higher the suitability of the test substance as the material for enhancing skin barrier function.

(4) The method of screening material for enhancing skin barrier function according to (3), wherein a type of the metal ions is calcium ion and/or magnesium ion.

(5) The method of screening material for enhancing skin barrier function according to (4), wherein the type of the metal ion is calcium ion.

(6) A material for enhancing skin barrier function, which is judged to be effective by the method of screening material for enhancing skin barrier function according to any one of (3) to (5).

(7) An adjuster for calcium ion in epidermis, comprising the material for enhancing skin barrier function according to (6).

(8) A cosmetic comprising the material for enhancing skin barrier function according to (6).

Advantageous Effects

According to the present invention, it is possible to provide a technology for developing an excellent material for enhancing skin barrier function, and to develop and provide a cosmetic having excellent ability to enhance the skin barrier function based on the technology.

BEST MODE FOR CARRYING OUT THE INVENTION

A method of evaluating skin barrier function is characterized by using permeability of metal ions through an epidermal cell layer as an index. The method uses permeability from a basal layer to a horny layer as the index. Note that the term "permeability" as used herein refers to both an ability of a substance to enter into and exit from cells and an ability of a substance to pass through cells. It is evaluated that the higher the permeability of the metal ions, the lower the skin barrier function.

The evaluating method, for example, can be performed as follows:

1) culturing normal human epidermal keratinocytes in wells with a semipermeable membrane bottom; 2) adding a medium not containing metal ions to be measured to the apical side of keratinocytes in each well and a medium containing the metal ions to be measured to the basolateral side of the keratinocytes in each well, provided that the basolateral side is a side where the keratinocytes are adhered to the semipermeable membrane, and the apical side is an opposite side thereto, and culturing the keratinocytes under metal ion loaded condition; 3) measuring a concentration of the metal ions in each medium; and 4) calculating permeability of the metal ions in an epidermal cell layer based on the measured concentrations of the media to evaluate the skin barrier function.

The epidermal cells may be epidermal cells of any sites, and examples thereof include a foreskin of a newborn baby and a breast of an adult woman. The epidermal cells may be commercially available epidermal cells. Examples of the commercially available epidermal cells include normal human newborn foreskin epidermal keratinocytes (NHEK) (manufactured by Kurabo Industries Ltd.). The epidermis is composed of a basal layer, a prickle cell layer, a granule layer, and a horny layer. In the evaluating method of the present invention, cells of all of the layers may be used, but basal layer cells are preferably used. The cell culture conditions or the like may be general conditions. The culture time under a metal ion loaded condition is generally about one to three hours. The concentration of loaded metal ions is generally about 5 to 10 mM.

Such evaluation may be performed in vitro for, e.g., three-dimensionally cultured epidermal cells as described above or for living experimental animals. Meanwhile, the evaluating method of the present invention may be used to uniformize a barrier function by measuring the value of the movement of metal ions for each prepared culture product to determine homogeneity.

As more developed application, the evaluating method of the present invention can be used for evaluating whether a test substance acts for enhancing or inhibiting skin barrier function in a formation of an epidermal cell membrane by comparing the cases of culture of normal human epidermal cells in presence and absence of the test substance.

From the viewpoint of improvement (strengthening) of skin barrier function, the evaluating method of the present invention can be applied to screening of a component for improving skin barrier function. For example, the screening can be performed by: defining a value calculated by the following expression: (1−metal ion permeation ratio in the presence of a test substance/metal ion permeation ration in the absence of a test substance)×100; and evaluating that the larger the value, the higher the ability to improve skin barrier function. The method can discriminate that the higher the ability to inhibit permeability of calcium or the like, the higher the ability to improve the skin barrier function. Such inhibition of permeation can control the concentration of ion such as calcium in the epidermis to correct the concentration gradient to an appropriate value. This promotes appropriate differentiation/maturation of epidermal/horny layer cells, resulting in improvement of barrier function of the horny layer. The screening described above may be performed by using normal epidermal cells derived from human or normal epidermal cells derived from an animal other than human. In addition, epidermal cells having specific properties are created by transforming the cells by masking a part of genes with complementary genes or introducing another gene into the cells using a vector or the like, and the epidermal cells may be used for the screening as in the above.

The metal ions to be used for the evaluation are not particularly limited as long as they are unevenly distributed in a living body, and are particularly preferably alkaline earth metals, and of those, a calcium and/or magnesium ion is preferred. Most preferred is a calcium ion. This is because the calcium ion acts as a cell differentiation factor in epidermal cells, and is a metal ion to be controlled in a condition that skin barrier function is normal, and excess permeation of the calcium ion in an epidermal cell layer is an absolute evidence of the skin barrier dysfunction. The efflux of the calcium ion from the epidermis, that is, excess passage of the calcium ion may prevent the maturation of horny layer cells and the formation of strong skin barrier function. A material to prevent such phenomenon can improve the barrier function in the epidermis and promote the maturation of healthy horny layer cells in a horny cell layer, resulting in improvement of the skin barrier function.

Means for qualitatively labeling such a metal ion has been known, and the labeling means may be used to clarify distribution of a metal ion such as a calcium ion in a living body. In the evaluating method of the present invention, such means may be employed. Examples of a preferable label for the calcium ion include a dye such as Arsenazo III or a salt thereof. Examples of a preferable label for a magnesium ion include Xylidyl blue I. The concentration of the label is 0.001 mM to 1,000 mM. An area where the label is localized is considered as an area where a metal ion such as calcium is also localized. In addition, an area where the concentration of the label is higher is considered as an area where the concentration of the metal ion such as a calcium ion is higher.

A material for enhancing skin barrier function of the present invention is a material for enhancing skin barrier function, which is judged to be effective by a method of screening material for enhancing the skin barrier function. The material is preferably includes a component that significantly inhibits the transference of calcium from the dermis, tissue equivalent for dermis, or deep part of the epidermis to the horny layer or tissue equivalent for horny layer in the presence of a test substance compared with the case in the absence of the test substance. Such an action is dose-dependent, and the material is preferably blended into a cosmetic in an amount within a range to give dose dependency. The dose for the action varies depending on type of materials, and is for example, 0.01 mM to 50 mM, and in terms of an animal or plant extract, 0.001 to 10% (final concentration in use). If the dose is within the range, the material can act as an adjuster for a calcium ion in the horny layer and improve the barrier function in the horny layer.

Specific preferred examples of the material for enhancing skin barrier function, which serves as an adjuster for a calcium ion, include: solvent-removed products or fractionated products of extracts obtained from peels of plants of the genus *Citrus* in the family Rutaceae such as orange, *Citrus tachibana*, and *Citrus aurantium* with a polar solvent, preferably an aqueous solution of 30 to 70% ethanol; solvent-removed products or fractionated products of extracts obtained from seeds of plants of the genus *Pimpinella* in the family Apiaceae such as Japanese honewort and fennel with a polar solvent, preferably an aqueous solution of 30 to 70% ethanol; extract, preferably, solvent-removed products or fractionated products of extracts obtained from flowers or flower buds of plants of the genus *Bellis* in the family Compositae such as *Bellis perennis* with a polar solvent, preferably an aqueous solution of 30 to 70% ethanol; royal jerry or a protein thereof, or a hydrolysate thereof; extract, preferably, solvent-removed products or fractionated products of extracts obtained from barks of plants of the genus *Fagus* in the family Fagaceae such as *Fagus crenata* Blume, *Fagus grandifolia* Ehrh, *Fagus japonica* Maxim, and *Fagus sylvatica*, preferably *Fagus sylvatica* with a polar solvent, preferably an aqueous solution of 30 to 70% ethanol; extract, preferably, solvent-removed products or fractionated products of extracts obtained from terrestial parts of plants of the genus *Chamerion in* the family Onagraceae such as *Epilobium angustifolium* with a polar solvent, preferably an aqueous solution of 30 to 70% ethanol; extract, preferably, solvent-removed products or fractionated products of extracts obtained from flowers or flower buds of *Capparis spinosa* of the family Capparidaceae with a polar solvent, preferably an aqueous solution of 30 to 70% ethanol; extracts obtained from bodies, preferably rhizome of plants of the genus *Coptis* in the family Ranunculaceae such as *Coptis japonica* MAKINO var. *japonica* SATAKE, *Coptis japonica* MAKINO var. *dissecta* NAKAI, and *Coptis japonica* (Makino) *Thunb*. var. *major* (*Miq.*) *Satake* with an aqueous solution of 30 to 70% ethanol, or optionally solvent-removed products or optionally fractionated products of the extracts; red alga extracts obtained by extracting red algae such as *Palmaria palmate* with water, adjusting molecular weights by ultrafiltration, if necessary, and removing the solvents; extract, preferably, solvent-removed products or fractionated products of extracts obtained from an echinoderm of the order Asterina in the class Asteroidea with a polar solvent, preferably an aqueous solution of 30 to 70% ethanol; and extract, preferably, solvent-removed products or fractionated products of extracts obtained from dried products of terrestial parts of plants of the genus *Houttuynia* in the family Saururaceae such as *Houttuynia cordata* with a polar solvent, preferably an aqueous solution of 30 to 70% ethanol.

Such a component is blended into a cosmetic in an amount of 0.01 to 10% by mass, more preferably 0.05 to 1% by mass based on the total amount of the cosmetic. The reason is as follows: if the amount is too small, the above-mentioned effects cannot be obtained in some cases, while if the amount is too large, the amount of the component delivered to the epidermis may reach a plateau, and freedom of the prescription may be unnecessarily impaired.

The cosmetic of the present invention is characterized by containing a strengthening material of the skin barrier function. The cosmetic of the present invention can contain optional ingredients used commonly in a cosmetic as well as those ingredients. Preferred examples of such an optional component include: oils/waxes such as *macadamia* nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as cetyl alcohol, stearyl alcohol, isostearyl alcohol, behenyl alcohol, octyldodecanol, myristyl alcohol, and cetostearyl alcohol; oil solutions of synthetic ester such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethyl hexanoate, neopentylglycol dicaprate, di-2-heptyl undecanoic acid glyceride, tri-2-ethylhexanoic acid glyceride, trimethylolpropane tri-2-ethylhexanoate, trimethylolpropane triisostearate, and pentaerythritol tetra-2-ethylhexanoate; chain polysiloxanes such as dimethylpolysiloxane, methylphenylpolysiloxane, and diphenylpolysiloxane; ring polyoxanes such as octamethylcyclotetrasiloxane, decamethylcyclopentasiloxane, and dodecamethylcyclohexanesiloxane; modified polysiloxanes including amino-modified polysiloxane, polyether-modified polysiloxane, alkyl-modified polysiloxane, and fluorine-modified polysiloxane; anionic surfactants such as fatty acid soaps (such as sodium laurate and sodium palmitate), potassium lauryl sulfate, and triethanolamine alkylsulfate ether; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazolinium hydroxide-1-carboxyethyloxy-2-sodium salt), betaine-based surfactants (such as alkyl betaine, amide betaine, and sulfo betaine), and acyl methyl taurine; nonionic surfactants such as sorbitan fatty acid esters (such as sorbitan monostearate and sorbitan sesquioleate), glycerol fatty acid esters (such as glycerin monostearate), propyleneglycol fatty acid esters (such as propyleneglycol monostearate), cured castor oil derivatives, glycerol alkylether, POE sorbitan fatty acid esters (such as POE sorbitan monooleate and polyoxyethylene sorbitan monostearate), POE sorbitol fatty acid esters (such as POE-sorbitol monolaurate), POE glycerol fatty acid esters (such as POE-glycerol monoisostearate), POE fatty acid esters (such as polyethyleneglycol monooleate and POE distearate), POE alkyl ethers (such as POE2-octyldodecyl ether), POE alkylphenyl ethers (such as POE nonylphenylether), pluronic types, POE/POP alkyl ethers (such as POE/POP2-decyltetradecyl ether), tetronic types, POE castor oil/cured castor oil derivatives (such as POE castor oil and POE cured castor oil), sucrose fatty acid ester, and alkyl glucoside; polyols such as polyethylene glycol, glycerol, 1,3-butylene glycol, erythritol, sorbitol, xylitol, maltitol, propylene glycol, dipropylene glycol, diglycerin, isoprene glycol, 1,2-pentanediol, 2,4-hexylene glycol, 1,2-hexanediol, and 1,2-octanediol; moisturizing components such as sodium pyrrolidone carboxylate, lactate, and sodium lactate; fine particles such as mica, talc, kaolin, synthetic mica, calcium carbonate, magnesium carbonate, silicic anhydride (silica), aluminum oxide, and barium sulfate, whose surfaces may be treated; inorganic pigments such as red iron oxide, yellow iron oxide, black iron oxide, cobalt oxide, ultramarine blue, iron blue, titanium oxide, and zinc oxide, whose surfaces may be treated; pearlescent pigments such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic fine particles such as polyethylene powder, polymethyl methacrylate powder, nylon powder, and organopolysiloxane elastomer; ultraviolet absorbents such as a p-aminobenzoate-based ultraviolet absorbent; an anthranilate-based ultraviolet absorbent; a salicylate-based ultraviolet absorbent; cinnamate-based ultraviolet absorbent; a benzophenone-based ultraviolet absorbent; a sugar-based ultraviolet absorbent; 2-(2'-hydroxy-5'-t-octylphenyl)benzotriazole, and 4-methoxy-4'-t-butyldibenzoylmethane; lower alcohols such as ethanol and isopropanol; vitamins such as vitamin A or derivatives thereof, vitamin B types such as vitamin B6 hydrochloride, vitamin B6 tripalmitate, vitamin B6 dioctanoate, vitamin B2 or derivatives thereof, vitamin B12, and vitamin B15 or derivatives thereof, vitamin E types such as α-tocopherol, β-tocopherol, γ-tocopherol, and vitamin E acetate, vitamin D types, vitamin H, pantothenic acid, pantethine, and pyrroloquinoline quinone; and antibacterial agents such as phenoxyethanol.

A cosmetic of the present invention can be produced by processing a material for enhancing skin barrier function, which is an essential component and serves as an adjuster for a calcium ion in the horny layer, together with the above-mentioned optional components in accordance with a conventional method. It is particularly preferable to accurately deliver the material for enhancing skin barrier function to the epidermis in an appropriate manner. Therefore, the material may be incorporated into a delivery compartment such as liposome, double-membrane vesicle, or fat globule such delivery compartment that carries a material for enhancing skin barrier function may be incorporated into a cosmetic. The cosmetic particularly preferably contains such a delivery compartment. Meanwhile, a formulation of the cosmetic is not particularly limited as long as it is generally known, and preferable examples of the cosmetic include lotion cosmetics, milky lotion cosmetics, cream cosmetics, essence cosmetics, pack cosmetics, under makeup cosmetics, and foundations, and of those, particularly preferable are lotion cosmetics, milky lotion cosmetics, cream cosmetics, essence cosmetics, pack cosmetics, etc.

EXAMPLES

Hereinafter, the present invention will be described in more detail with reference to examples, but it will be obvious that the present invention is not limited to the examples.

Example 1

An ion permeability test using normal human epidermal cells was performed based on a method of evaluating skin barrier function of the present invention.

1) Cell Inoculation and Ion Permeability Experiment

Frozen normal human epidermal keratinocytes (NHEK) (manufactured by Kurabo Industries Ltd.) were thawed and cultured in a 0.15 mM Ca-containing culture medium (Humedia-KG2; manufactured by Kurabo Industries Ltd.) at 37° C. in 50% carbon dioxide atmosphere. A Transwell (registered trademark) manufactured by Corning Incorporated (diameter 12 mm, polyethylene terephthalate, 0.4 µm pore) was placed on a Millicell (registered trademark) tissue culture plate (manufactured by Millipore), and the above-mentioned culture medium was added in amounts of 1.5 ml to the lower layer and 0.5 ml to the upper layer. Then, the normal human epidermal keratinocytes (NHEK) were inoculated at $1\times10^5$/$cm^2$ and cultured for additional 72 hours. After the cells were confirmed to be confluent, the culture medium was exchanged for a 1.45-mM Ca-containing Humedia KG2 medium, and the cells were cultured for additional 96 hours. When TERs (transepithelial electrical resistance) reach the peak (350 to 450Ω·$cm^2$), and the prepared solutions described in Table 1 were each added to the basolateral side in an amount of 1.5 ml, and the prepared solutions described in Table 1 were each added to the apical side in an amount of 0.5 ml. Static cultures were each performed at 37° C. in 5% carbon dioxide atmosphere for two hours, and the solutions of the apical and basolateral sides were each recovered.

TABLE 1-1

| | Solutions for $Ca^{2+}$ permeation experiments | | | | | | |
|---|---|---|---|---|---|---|---|
| | apical soln. | basal soln. (f.c.) | | | | | |
| | (f.c.) | (a) | (b) | (c) | (d) | (e) | (f) |
| $MgCl_2$ | 1 mM | | | | 1 mM | | |
| glucose | 10 mM | | | | 10 mM | | |
| HEPES | 10 mM (pH 7.4) | | | | 10 mM (pH 7.4) | | |
| Mannitol | 280 mM | — | 130 mM | 220 mM | 250 mM | 265 mM | 274 mM |
| $CaCl_2$ | — | 100 mM | 50 mM | 20 mM | 10 mM | 5 mM | 2 mM |

TABLE 1-2

Solutions for $Mg^{2+}$ permeation experiments

| | apical soln. (f.c.) | basal soln. (f.c.) | | | | | |
|---|---|---|---|---|---|---|---|
| | | (a) | (b) | (c) | (d) | (e) | (f) |
| $CaCl_2$ | 1 mM | | | | 1 mM | | |
| glucose | 10 mM | | | | 10 mM | | |
| HEPES | 10 mM (pH 7.4) | | | 10 mM (pH 7.4) | | | |
| Mannitol | 280 mM | — | 130 mM | 220 mM | 250 mM | 265 mM | 274 mM |
| $MgCl_2$ | — | 100 mM | 50 mM | 20 mM | 10 mM | 5 mM | 2 mM |

2) Ion Permeability Coefficient Calculation Formula

The recovered samples were quantified with quantification reagents {Ca-Arsenazo-III, Mg-Xylidyl blue I (both are manufactured by Fluka)}. The quantification flow is shown below. The net flux (mass transfer per unit time and unit area) was calculated from the quantification results, and Ca and Mg ion permeability coefficients were calculated by the following formula.

$$P(\text{nmol/mM/h/cm}^2) = \frac{NetFlux(\text{nmol/h/cm}^2)}{C_{basolateral}(\text{mM})} \quad \text{Formula 1}$$

3) Ca Quantification a) 7.76 mg of Arsenazo III was dissolved in 100 μl of 1N NaOH, and the volume of the solution was adjusted to 50 ml with the apical solution for Ca prepared in Table 1 (Ca quantification solution).

b) An aqueous solution of 1M $CaCl_2$ was diluted with the apical solution to prepare 0.01 to 1 mM Ca-standard solutions, and the Ca-standard solutions and Ca quantification solution were each added to a 96-well plate in an amount of 50 μl/well to measure ODs (600), followed by creation of a calibration curve.

c) In order to quantify Ca in a sample, the Ca quantification solution and the sample were each added to the plate in an amount of 50 μl/well to measure ODs (600). If the resultant value was above the range of the calibration curve, the sample was diluted with the apical solution.

4) Mg Quantification a) 5.13 mg of Xylidyl blue I was dissolved in 200 μl of 1N NaOH, and the volume of the solution was adjusted to 50 ml with a borate buffer (prepared by mixing 40 ml of 0.2 mol/l NaOH, 0.2 mol/l KCl, and 50 ml of a $H_3BO_3$ mix solution (15 g of KCl and 12.5 g of $H_3BO_3$ were dissolved into distilled water to be adjusted to 1 l), pH 10). (Mg quantification solution)

b) An aqueous solution of 1M $MgCl_2$ was diluted with the apical solution to prepare 0.01 to 1 mM Mg-standard solutions, and the Mg-standard solutions (15 μl/well) and the Mg quantification solution (100 μl/well) were added to a 96-well plate to measure ODs (520), followed by creation of a calibration curve.

c) In order to quantify Mg in a sample, the Mg quantification solution (15 μl/well) and the sample (100 μl/well) were added to the plate to measure ODs (520). If the resultant value was above the range of the calibration curve, the sample was diluted with the apical solution before measurement.

5) Correlation between TER and Permeability Coefficient

Frozen normal human epidermal keratinocytes (NHEK) (manufactured by Kurabo Industries Ltd.) were thawed and cultured in a 0.15 mM Ca-containing culture medium (Humedia-KG2; manufactured by Kurabo Industries Ltd.) at 37° C. in 50% carbon dioxide atmosphere. A Transwell (registered trademark) manufactured by Corning Incorporated (diameter 12 mm, polyethylene terephthalate, 0.4 μm pore) was placed on a Millicell (registered trademark) tissue culture plate (manufactured by Millipore), and the above-mentioned culture medium was added in amounts of 1.5 ml to the lower layer and 0.5 ml to the upper layer. Then, the normal human epidermal keratinocytes (NHEK) were inoculated at $1×10^5$/$cm^2$ and cultured for additional 72 hours. After the cells were confirmed to be confluent, the culture medium was exchanged for a 1.45 mM Ca-containing Humedia KG2 medium, and the cells were cultured for additional 96 hours. TERs were measured, and the prepared solution described in Table 1-1(e) or Table 1-2 (e) was added to the basolateral side in an amount of 1.5 ml, and the prepared solution described in Table 1-1 or Table 1-2 was each added to the apical side in an amount of 0.5 ml. Static cultures were each performed at 37° C. in 5% carbon dioxide atmosphere for two hours, and the solutions of the apical and basolateral sides were each recovered, followed by measurement of ion permeability coefficients. After the measurement, the medium was exchanged for a 1.45 mM Ca-containing Humedia KG2 medium, and one and two days later, TERs and ion permeability coefficients were measured by the same procedures as above.

6) Results

Figure 1:
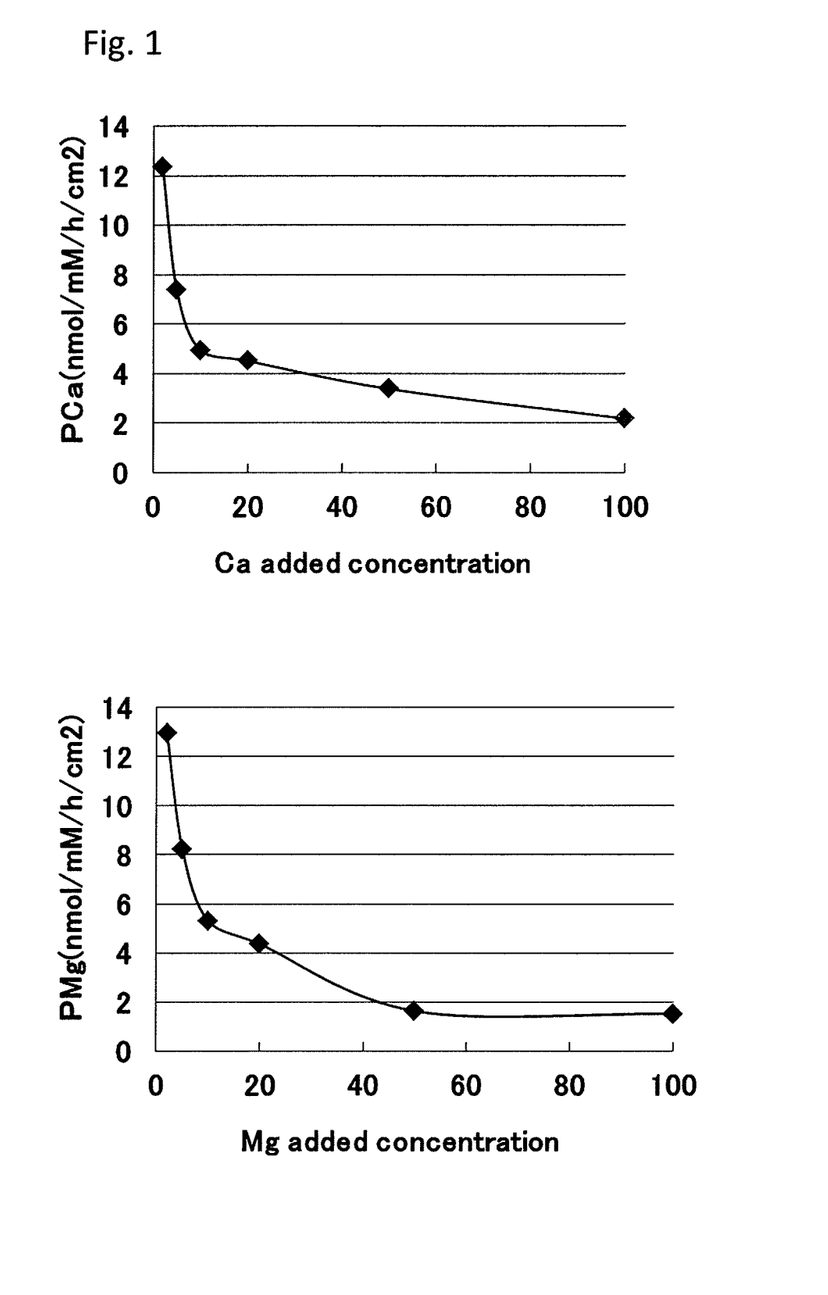
FIG. 1 Graphs each showing a relationship between an added metal ion concentration and a permeability coefficient obtained in Example 1.
Figure 2:
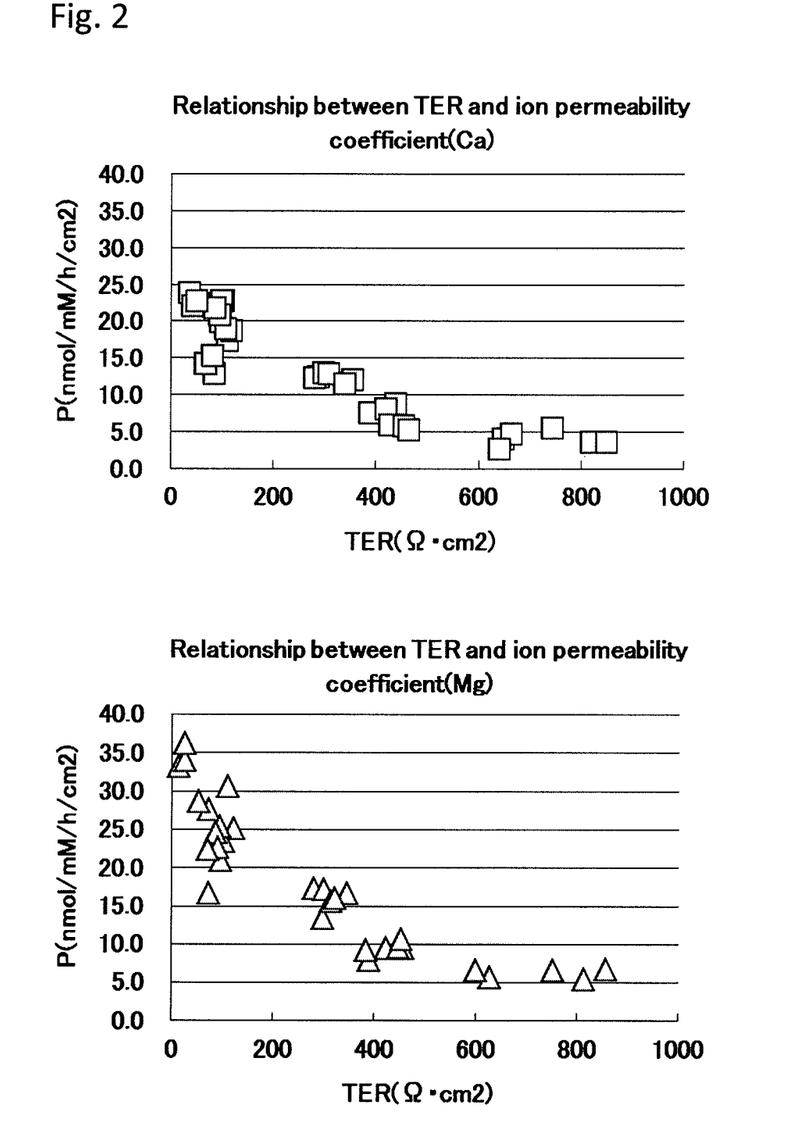
FIG. 2 Graphs each showing a relationship between TER and the permeability coefficient obtained in Example 1.

Relationships between added metal ion concentrations and permeability coefficients are shown in FIG. 1. The results revealed that the permeability coefficients were significantly high at concentrations of 5 mM or less, so it was found that, if metal ion loaded concentrations are set within the range, the influences can be evaluated more clearly. In addition, TERs were found to be negatively correlated with permeability coefficients, and the fact supports that the permeability coefficients are values correlated with skin barrier function. The results are shown in FIG. 2.

Example 2

Figure 3:
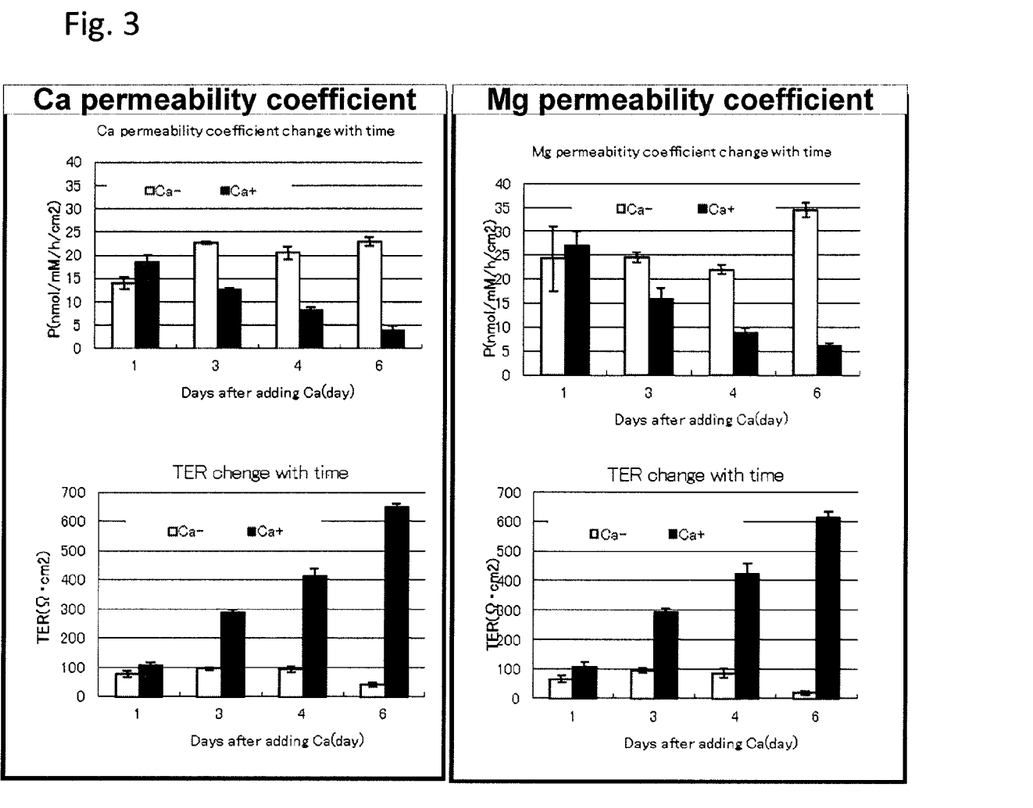
FIG. 3 Graphs each showing a comparison result of media obtained in Example 2.

In the same way as in Example 1, calcium was selected as a metal ion to be added to compare calcium permeability coefficients and magnesium permeability coefficients in a low-calcium medium cultured cells (shown as Ca− in FIG. 3) (0.15 mM) and in a high-calcium medium cultured cells (shown as $Ca^+$ in FIG. 3) (1.45 mM). That is, frozen normal human epidermal keratinocytes (NHEK) (manufactured by Kurabo Industries Ltd.) were thawed and cultured in a 0.15 mM Ca-containing culture medium (Humedia-KG2; manufactured by Kurabo Industries Ltd.) at 37° C. in 50% carbon dioxide atmosphere. A Transwell (registered trademark) manufactured by Corning Incorporated (diameter 12 mm, polyethylene terephthalate, 0.4 μm pore) was placed on a Millicell (registered trademark) tissue culture plate (manufactured by Millipore), and the above-mentioned culture medium was added in amounts of 1.5 ml to the lower layer and 0.5 ml to the upper layer. Then, the normal human epidermal keratinocytes (NHEK) were inoculated at $1 \times 10^5/cm^2$ and cultured for additional 72 hours. After the cells were confirmed to be confluent, in the case of the low-calcium medium, Humedia-KG2 medium was not exchanged, while in the case of the high-calcium medium, the culture medium was exchanged for a 1.45 mM Ca-containing Humedia KG2 medium, and the cells were further cultured. One day later, TERs were measured, and the prepared solution described in Table 1-1(e) or Table 1-2 (e) was added to the basolateral side in an amount of 1.5 ml, and the prepared solution described in Table 1-1 or Table 1-2 was each added to the apical side in an amount of 0.5 ml. Static cultures were each performed at 37° C. in 5% carbon dioxide atmosphere for two hours, and the solutions of the apical and basolateral sides were each recovered, followed by measurement of ion permeability coefficients. After the measurement, the medium was exchanged for Humedia-KG2 medium or a 1.45 mM Ca-containing Humedia KG2 medium, and one to five days later, TERs and ion permeability coefficients were measured by the same procedures as above. The results are shown in FIG. 3. The results revealed that, in the keratinocytes grown in the high-calcium medium, with progress in the formation of tight junctions, the TERs increase and ion permeability coefficients decrease. This supports that calcium acts as an index of skin barrier function and affects the formation of cell membranes, that is, affects the skin barrier itself, and control of its permeability is important for considering the skin barrier function.

Example 3

Figure 4:
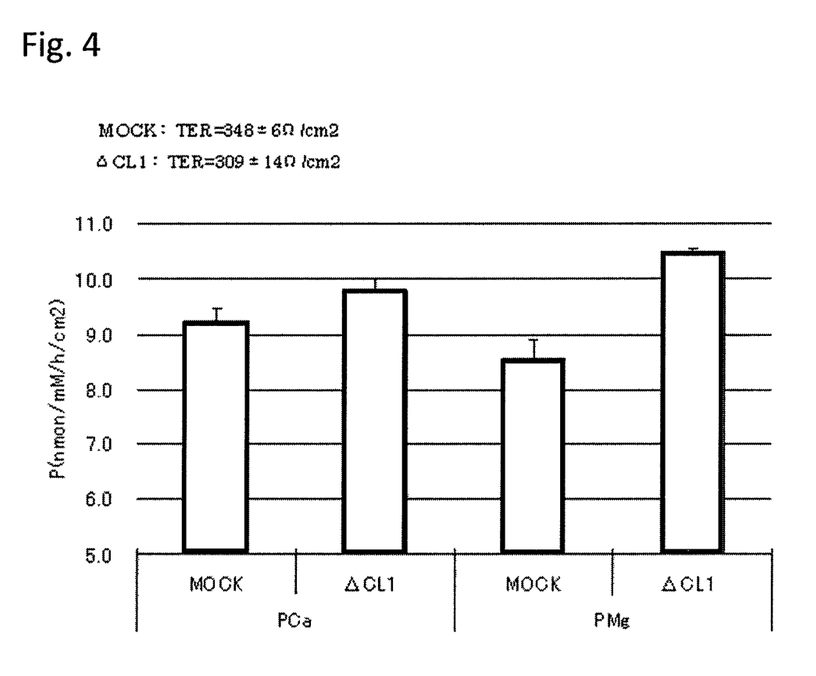
FIG. 4 A graph showing results according to Example 3.

TERs and metal ion permeability coefficients in the case where claudin-1, one of tight junction proteins serving as adhesion factors for epidermal cells, was suppressed with siRNA were measured in accordance with the method of Example 1. That is, frozen normal human epidermal keratinocytes (NHEK) (manufactured by Kurabo Industries Ltd.) were thawed and cultured in a 0.15 mM Ca-containing culture medium (Humedia-KG2; manufactured by Kurabo Industries Ltd.) at 37° C. in 50% carbon dioxide atmosphere. Thereafter, siRNA was transfected into the cultured cells. A Transwell (registered trademark) manufactured by Corning Incorporated (diameter 12 mm, polyethylene terephthalate, 0.4 μm pore) was placed on a Millicell (registered trademark) tissue culture plate (manufactured by Millipore), and the above-mentioned culture medium was added in amounts of 1.5 ml to the lower layer and 0.5 ml to the upper layer. Then, the human epidermal keratinocytes transfected with siRNA were inoculated at $2.5 \times 10^5/cm^2$ and cultured for additional 24 hours. After the cells were confirmed to be confluent, the culture medium was exchanged for a 1.45 mM Ca-containing Humedia KG2 medium, and the cells were cultured for 48 hours. TERs were measured, and the prepared solution described in Table 1-1(e) or Table 1-2 (e) was added to the basolateral side in an amount of 1.5 ml, and the prepared solution described in Table 1-1 or Table 1-2 was each added to the apical side in an amount of 0.5 ml. Static cultures were each performed at 37° C. in 5% carbon dioxide atmosphere for two hours, and the solutions of the apical and basolateral sides were each recovered, followed by measurement of ion permeability coefficients. The results are shown in FIG. 4. The results revealed that when claudin-1 is suppressed, the TERs decrease and the permeability coefficients of metal ions such as calcium and magnesium increase. This suggested that a tight junction protein such as claudin-1 affected permeation of the metal ions, thereby affecting the skin barrier function.

Example 4

Figure 5:
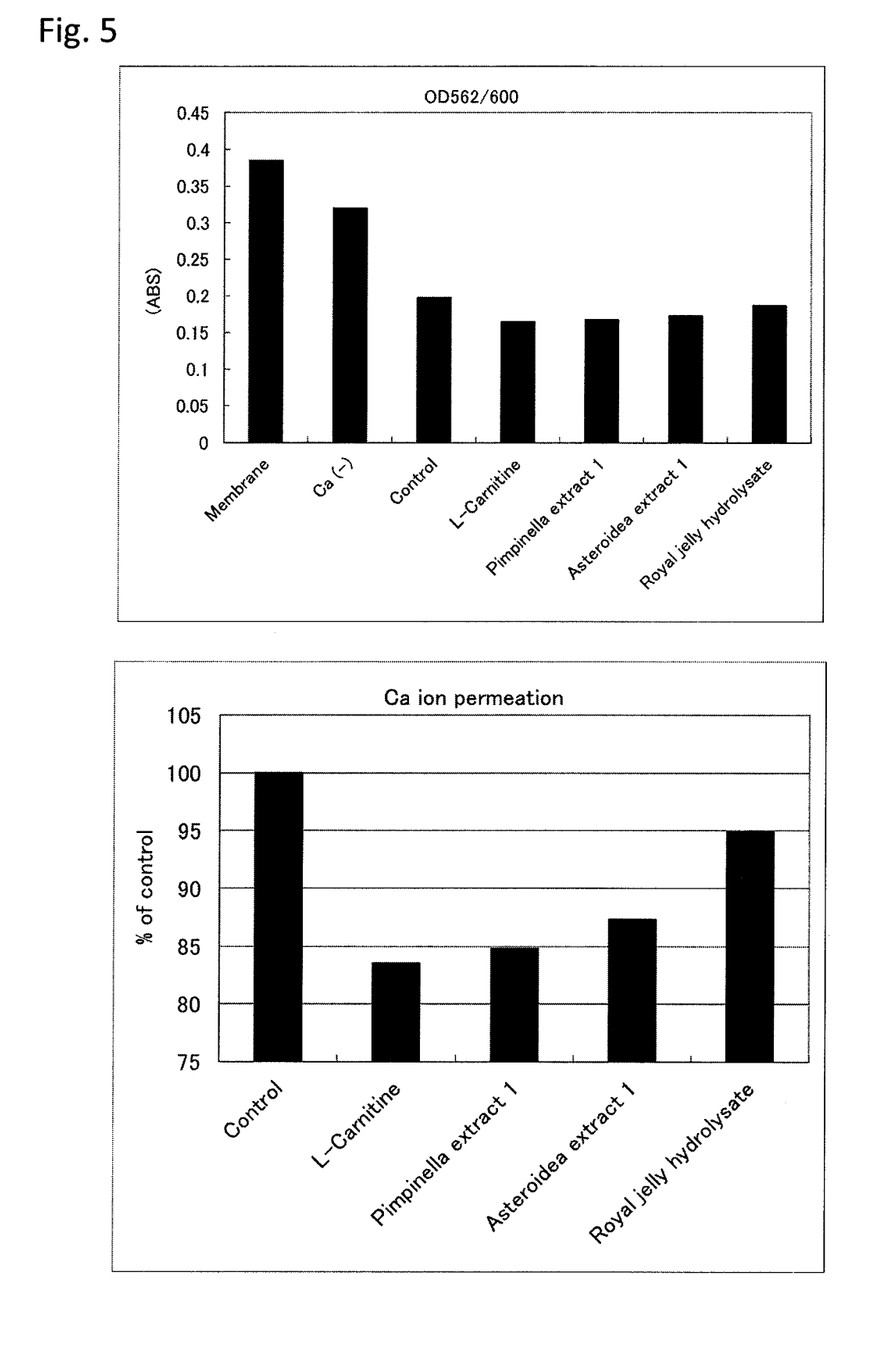
FIG. 5 Graphs each showing results according to Examples 4 to 7.

3 l of an aqueous solution of 50% ethanol was added to 500 g of pulverized seeds of a plant of the genus *Pimpinella* in the family Apiaceae, and the mixture was heated with stirring to perform reflux for three hours. After cooling to room temperature, insoluble matters were removed by filtration, and the filtrate was concentrated under reduced pressure. 1 l of water and 1 l of ethyl acetate were added to the residue to perform liquid-liquid extraction. The ethyl acetate layer was collected, washed with 500 ml of water twice, dried with anhydrous sodium sulfate, and concentrated under reduced pressure, and the solvent was removed, to thereby yield a *Pimpinella* extract 1. Cells obtained by three-dimensional culture by the procedure of Example 1-1) were cultured in the presence of $10^{-1}\%$ of the *Pimpinella* extract 1 at a calcium loaded concentration of 5 mM, and a calcium ion was stained by the procedure of Example 1-3) and an absorbance was measured. A test substance having a concentration of 0 was defined as a control, and a calcium ion permeation ratio was calculated. The results are shown in FIG. 5. The results revealed that *Pimpinella* extract 1 had ability to inhibit the transference of a calcium ion from the dermis/the deep part of the epidermis to the horny cell layer.

Example 5

To study inhibition of the transference of a calcium ion, the same procedure as in Example 4 was repeated except that L-carnitine (manufactured by Sigma) was used instead of the *Pimpinella* extract 1. The results are shown in FIG. 5. The results revealed that L-carnitine had ability to inhibit the transference of a calcium ion from the dermis/the deep part of the epidermis to the horny cell layer.

Example 6

3 l of water was added to 500 g of a dried product of an echinoderm of the order Asterina in the class Asteroidea, and the mixture was heated with stirring to perform reflux for three hours. After cooling to room temperature, insoluble matters were removed by filtration, and the filtrate was concentrated under reduced pressure, to thereby yield an *Asteroidea* extract 1. To study inhibition of the transference of a calcium ion, the same procedure as in Example 4 was repeated except that the Asteroidea extract 1 was used instead of the *Pimpinella* extract 1. The results are shown in FIG. 5. The results revealed that the Asteroidea extract 1 had ability to inhibit the transference of calcium ion from the dermis/the deep part of the epidermis to the horny cell layer.

Example 7

To study inhibition of the transference of a calcium ion, the same procedure as in Example 4 was repeated except that hydrolyzed royal jelly protein ("Royal Biocyte PX", manufactured by Katakura Chikkarin Co., Ltd.) was used instead of the *Pimpinella* extract 1. The results are shown in FIG. 5. The results revealed that the hydrolyzed royal jelly protein had ability to inhibit the transference of a calcium ion from the dermis/the deep part of the epidermis to the horny cell layer.

Example 8

Figure 6:
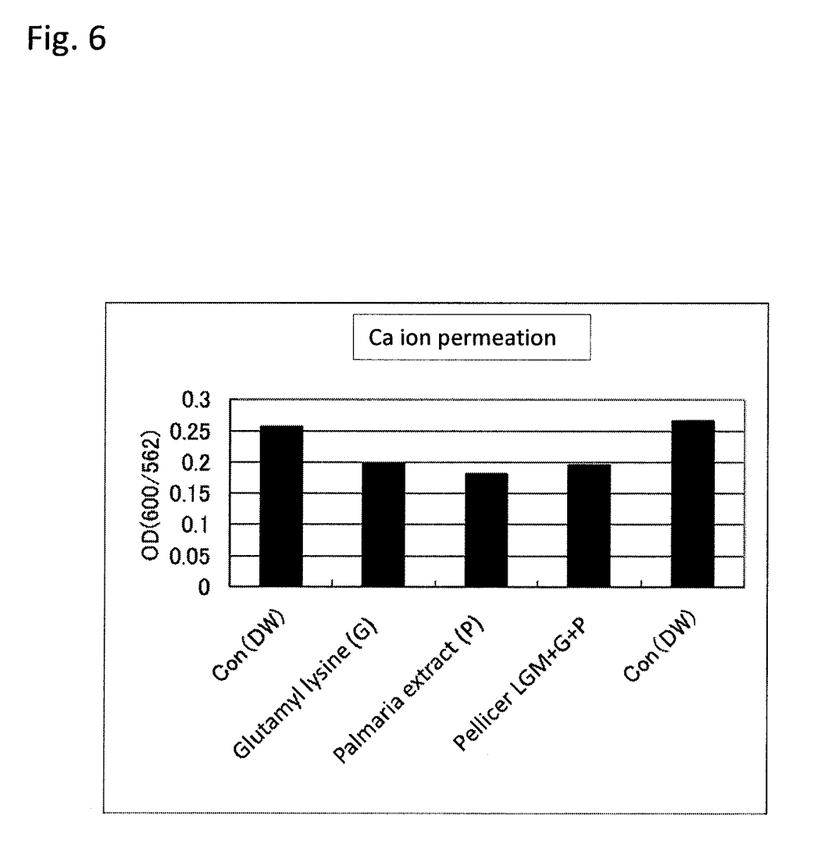
FIG. 6 A graph showing results according to Examples 8, 10, and 11.

The whole plant body of Palmaria palmate was dried, and 100 g of the dried product was weighed. 2 l of water was added to the product, and the mixture was gradually heated up to 60° C. The temperature was maintained for three hours, and the mixture was cooled to room temperature. After cooling, insoluble matters were removed by filtration, and the filtrate was freeze-dried, to thereby yield a Palmaria extract 1. To study inhibition of the transference of a calcium ion, the same procedure as in Example 4 was repeated except that the Palmaria extract 1 was used instead of the *Pimpinella* extract 1. The results are shown in FIG. 6. The results revealed that the Palmaria extract 1 had ability to inhibit the transference of a calcium ion from the dermis/the deep part of the epidermis to the horny cell layer.

Example 9

Figure 7:
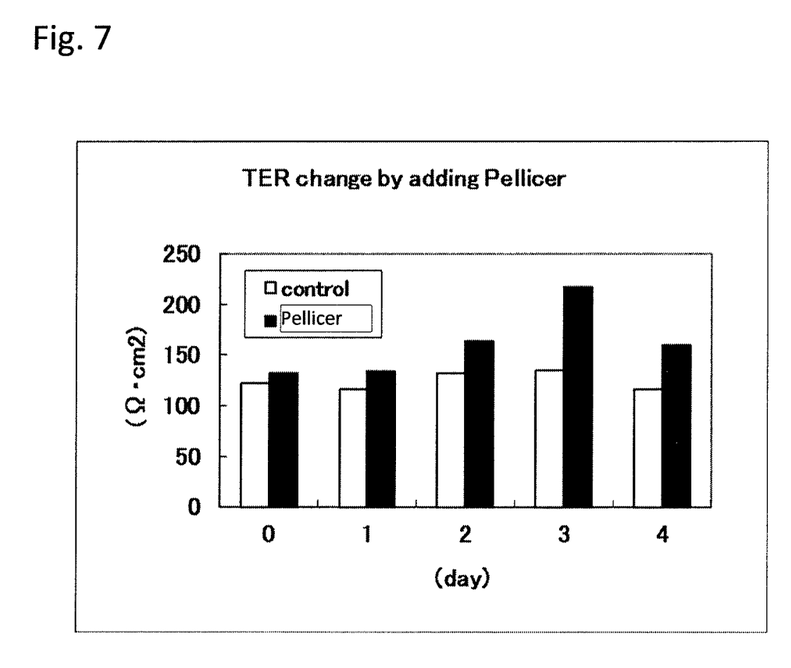
FIG. 7 A graph showing results according to Example 9.

Frozen normal human epidermal keratinocytes (NHEK) (manufactured by Kurabo Industries Ltd.) were thawed and cultured in a 0.15 mM Ca-containing culture medium (Humedia-KG2; manufactured by Kurabo Industries Ltd.) at 37° C. in 50% carbon dioxide atmosphere. A Transwell manufactured by Corning Incorporated (diameter 12 mm, polyethylene terephthalate, 0.4 μm pore) was placed on a Millicell tissue culture plate (manufactured by Millipore), and the above-mentioned culture medium was added in amounts of 0.5 ml to the upper layer and 1.5 ml to the lower layer. Then, the normal human epidermal keratinocytes (NHEK) were inoculated at $1\times10^5/cm^2$ and cultured for additional 72 hours. After the cells were confirmed to be confluent, the culture medium was exchanged for a 1.45 mM Ca-containing Humedia KG2 medium, and the cells were cultured for additional 96 hours. Thereafter, the medium was exchanged for a culture medium containing $10^{-4}$ v/v % α,ε-bis(γ-N-lauroylglutamyl)lysine (Pellicer L-30 (registered trademark) (hereinafter, referred to as Pellicer); manufactured by Asahi Kasei Corporation), and TERs were measured. The culture was further continued, and one, two, three, and four days later, TERs were measured. The graph shows changes with time in TER (transepitherial electrical resistance) values ($\Omega \cdot cm^2$) after certain lengths of time with respect to TER values at the time of addition of the extract. The results are shown in FIG. 7. In addition, calcium ion permeability coefficients were measured in accordance with the procedure of Example 1, and it was found that the coefficients were inversely correlated with the changes in the TERs. The results revealed that addition of Pellicer inhibited the transference of a calcium ion and provided an increased resistance value compared with the control.

Example 10

To study inhibition of the transference of a calcium ion, the same procedure as in Example 4 was repeated except that ε,γ-glutamyl lysine was used instead of the *Pimpinella* extract 1. The results are shown in FIG. 6. The results revealed that ε,γ-glutamyl lysine had ability to inhibit the transference of the calcium ion from the dermis/the deep part of the epidermis to the horny cell layer.

Example 11

Effects of combination use of the Palmaria extract 1, α,ε-bis(γ-N-lauroylglutamyl)lysine (Pellicer), and ε,γ-glutamyl lysine were determined in the same as above. The results are shown in FIG. 6. The effects of combination use were confirmed.

Example 12

3 l of an aqueous solution of 50% ethanol was added to 500 g of rhizome pieces of *Coptis japonica* of the genus *Coptis* in the family Ranunculaceae, and the mixture was heated with stirring to perform reflux for three hours. After cooling to room temperature, insoluble matters were removed by filtration, and the filtrate was concentrated under reduced pressure. 1 l of water and 1 l of ethyl acetate were added to the residue to perform liquid-liquid extraction. The ethyl acetate layer was collected, washed with 500 ml of water twice, dried with anhydrous sodium sulfate, and concentrated under reduced pressure, and the solvent was removed, to thereby yield a *Coptis japonica* extract 1.

Figure 8:
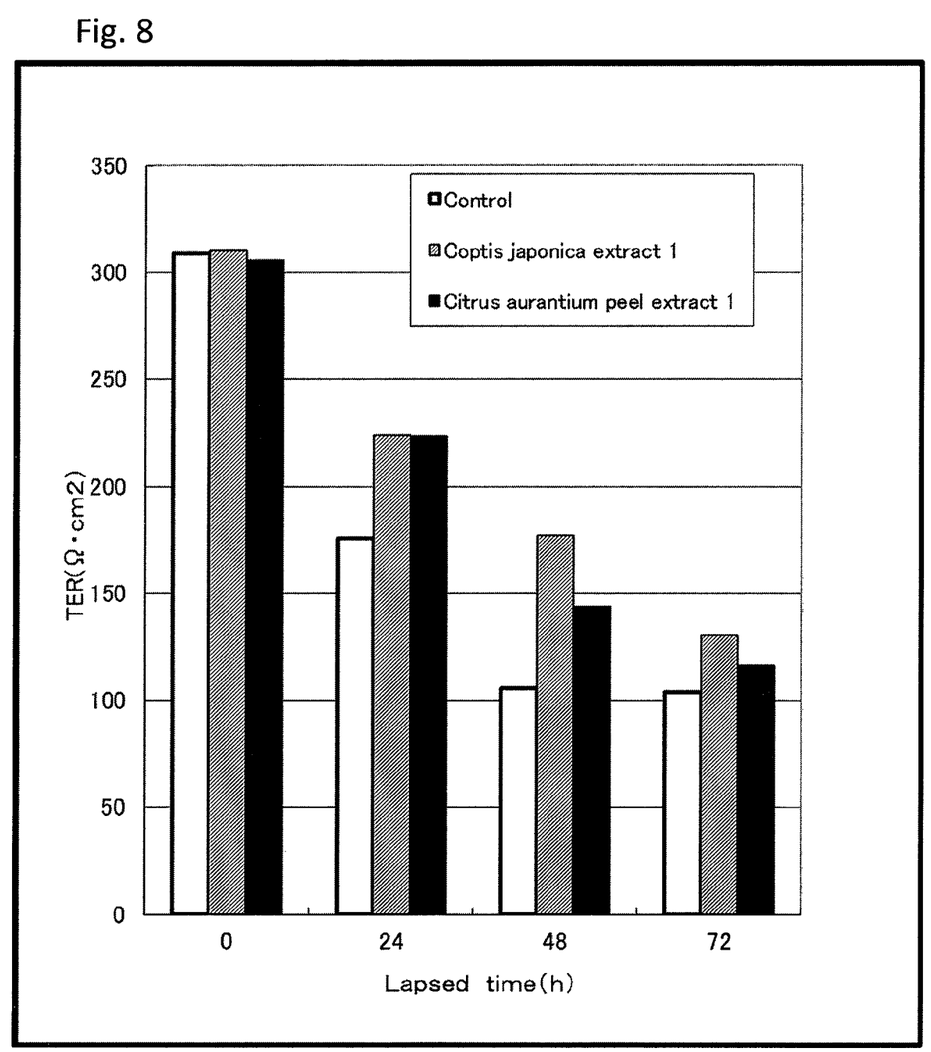
FIG. 8 A graph showing the results of Examples 12 and 13.

Frozen normal human epidermal keratinocytes (NHEK) (manufactured by Kurabo Industries Ltd.) were thawed and cultured in a 0.15 mM Ca-containing culture medium (Humedia-KG2; manufactured by Kurabo Industries Ltd.) at 37° C. in 50% carbon dioxide atmosphere. A Transwell manufactured by Corning Incorporated (diameter 12 mm, polyethylene terephthalate, 0.4 μm pore) was placed on a Millicell tissue culture plate (manufactured by Millipore), and the above-mentioned culture medium was added in amounts of 0.5 ml to the upper layer and 1.5 ml to the lower layer. Then, the normal human epidermal keratinocytes (NHEK) were inoculated at $1\times10^5/cm^2$ and cultured for additional 72 hours. After the cells were confirmed to be confluent, the culture medium was exchanged for a 1.45 mM Ca-containing Humedia KG2 medium, and the cells were cultured for additional 96 hours. Thereafter, the medium was exchanged for a culture medium containing $10^{-5}$ v/v % the *Coptis japonica* extract 1, and TERs were measured. The culture was further continued, and one, two, three, and four days later, TERs were measured. The graph shows changes with time in TER (transepithelial electrical resistance) values ($\Omega \cdot cm^2$) after certain lengths of time with respect to TER values at the time of addition of the extract. The results are shown in FIG. 8. In addition, calcium ion permeability coefficients were measured in accordance with the procedure of Example 1, and it was found that the coefficients were inversely correlated with the changes in the TERs. The results revealed that addition of the *Coptis japonica* extract 1 inhibited the transference of the calcium ion and provided an increased resistance value compared with the control.

Example 13

The same procedure as in Example 12 was repeated except that a dried product of the peel of *Citrus aurantium* of the genus *Citrus* in the family Rutaceae was used instead of the rhizome of *Coptis japonica*, to thereby yield a *Citrus aurantium* peel extract 1. The extract was evaluated by measuring changes in resistance values caused by inhibition of the transference of the calcium ion in the same way as in Example 12. The results are shown in FIG. 8. The results revealed that the *Citrus aurantium* peel extract 1 had excellent ability to inhibit calcium.

Example 14

According to the following prescriptions, a cosmetic of the present invention was produced. Specifically, according to the following prescriptions, cosmetic of the present invention was prepared as milky lotions. That is, the components shown in (A) were mixed and heated to 80° C. On the other hand, the components shown in (B) were heated to 80° C. The mixture (B) was added to the mixture (A), and the whole was emulsified by stirring and neutralized by adding the components shown in (C), followed by cooling to 35° C. with stirring, to thereby prepare a milky lotion.

TABLE 2

| Components | % by mass |
|---|---|
| (A) | |
| Behenyl alcohol | 0.5 |
| Cetyl isooctanate | 2.0 |
| Squalane | 8.0 |
| Dimethicone | 2.0 |
| Sorbitan sesquistearate | 1.5 |
| PEG-45 stearate | 1.0 |
| Cetyl stearate | 0.5 |
| Behenic acid | 0.5 |
| (B) | |
| 1,3-Butanediol | 5.0 |
| Glycerol | 5.0 |
| 1,2-Octanediol | 1.0 |
| Pure water | 50.0 |
| Components described in Table 3 | 0.5 |
| Dipotassium glycyrrhizinate | 0.1 |
| (C) | |
| Pure water | 21.8 |
| Potassium hydroxide | 0.6 |
| Total | 100 |

TABLE 3

| Milky lotions | Components |
|---|---|
| Milky lotion 1 | *Pimpinella* extract 1 |
| Milky lotion 2 | *Asteroidea* extract 1 |
| Milky lotion 3 | L-Carnitine |
| Milky lotion 4 | Royal jelly hydrolysate |
| Milky lotion 5 | Pellicer |
| Milky lotion 6 | *Palmaria* extract 1 |
| Milky lotion 7 | ε,γ-Glutamyl lysine |
| Milky lotion 8 | *Coptis japonica* extract 1 |
| Milky lotion 9 | *Citrus aurantium* peel extract 1 |

[Industrial Applicability]

The present invention can be applied to design of a cosmetic or the like.

What is claimed is:

1. A method for adjusting calcium ion in epidermis, comprising applying a material for enhancing skin barrier function to the skin of a subject in need thereof, wherein the material is α, ε-bis(γ-N-lauroylglutamyl)lysine.

* * * * *